United States Patent [19]

Tanberg

[11] Patent Number: 4,610,845
[45] Date of Patent: Sep. 9, 1986

[54] SYSTEM FOR TESTING CHEMICALS BEFORE MIXING THEM TO AVOID RUN-AWAY REACTIONS

[75] Inventor: Dennis A. Tanberg, Lake Jackson, Tex.

[73] Assignee: The Dow Chemical Company, Midland, Mich.

[21] Appl. No.: 437,662

[22] Filed: Oct. 29, 1982

[51] Int. Cl.⁴ ............................................. G01N 25/20
[52] U.S. Cl. ........................................ 422/51; 374/31; 422/62; 422/117; 436/174
[58] Field of Search ................... 422/51, 62, 117, 119, 422/111, 109, 230, 231; 374/31, 36, 37; 436/147; 210/241, 96.1

[56] References Cited

U.S. PATENT DOCUMENTS 3,080,219  3/1963  Harvey .................................. 422/109
3,138,436  6/1964  Harmon .......................... 436/147 X
3,726,644  4/1973  Desnoyers et al. ................ 422/51 X
4,130,016 12/1978  Walker ................................ 436/147

FOREIGN PATENT DOCUMENTS 695623   8/1953  United Kingdom .............. 210/96.1
1217325 12/1970  United Kingdom ................ 436/147

OTHER PUBLICATIONS

Chemical Abstracts, vol. 94, #213986d, A Method for Determining the Compatibility of Hazardous Wastes.

Primary Examiner—Arnold Turk
Attorney, Agent, or Firm—M. W. Barrow

[57] ABSTRACT

Method and apparatus system for quickly determining on site if chemicals which are to be mixed can be done so safely without having a run-away exothermal reaction take place and without exposing personnel to the chemicals. The invention is particularly useful in dumping quantities of waste chemicals into a waste chemical reservoir containing a very complex mixture of many other waste chemicals.

3 Claims, 3 Drawing Figures

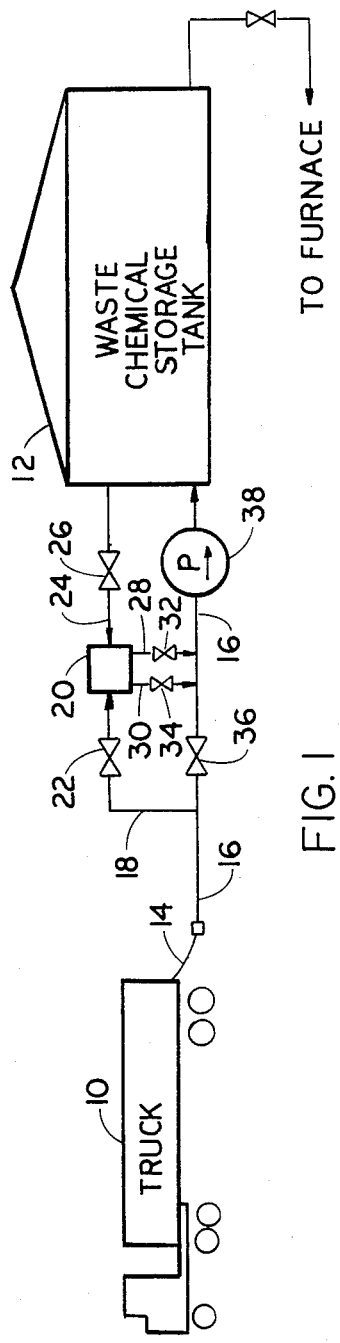
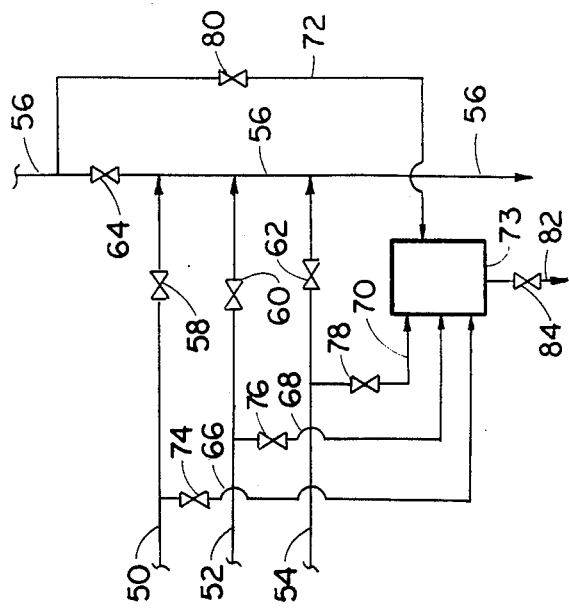
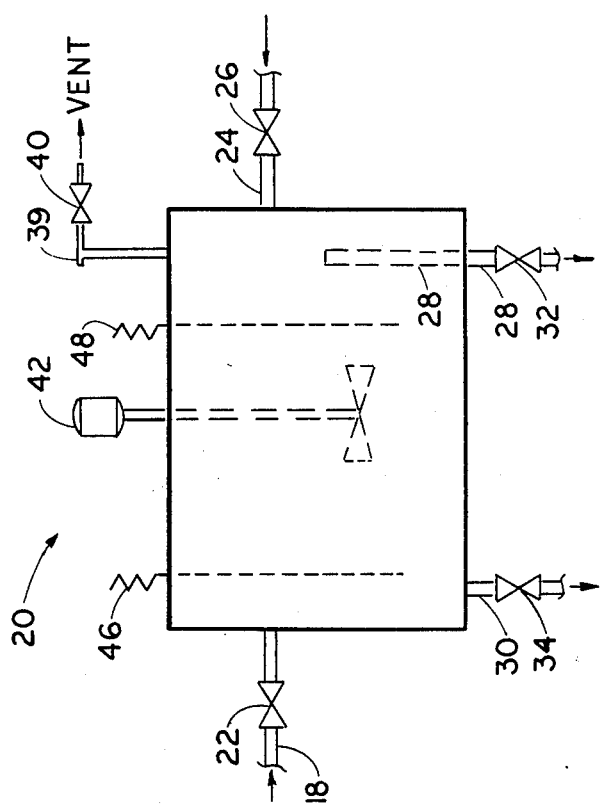
FIG. 1
FIG. 2
FIG. 3

SYSTEM FOR TESTING CHEMICALS BEFORE MIXING THEM TO AVOID RUN-AWAY REACTIONS

BACKGROUND OF THE INVENTION

This invention relates to checking chemicals before mixing them to determine if upon their mixing they will initiate a run-away exothermic reaction. The invention is particularly useful when emptying waste inorganic and catalytic chemicals into a chemical waste depository containing many chemicals in a mix whose reactivity with the waste chemicals to be dumped is unknown. Under these latter conditions it has been very tedious and often dangerous to personnel to determine if the resulting mixture will not be the source of a run-away exothermic reaction; i.e., an explosion or fire. This is particularly true when there have been many (e.g., 30 to 40) chemicals added to the chemical waste depository prior to adding another chemical. The uncertainty is great as to whether the resulting new mixture will be safe or not. Particularly is this true when there are organic chemicals and/or chemical catalytic agents present.

Ordinarily to determine if such resulting mixtures were going to be safe, compatibility tests for the many individual chemicals or groups of chemicals present were run at a remote site in a chemical laboratory. Necessarily this was quite time consuming. Furthermore it exposed personnel to what may well be noxious or poisonous chemicals.

The present invention avoids these and other problems by providing a quick simple test at the dump site.

Also not to be overlooked is the use of this invention in connection with testing non-waste chemicals which are desired to be mixed and/or reacted together. This invention can provide quick checks upon such chemicals to determine if their resulting mixture is a safe and controllable mixture or reaction mixture.

SUMMARY OF THE INVENTION

This invention is an improved method and apparatus system for determining if chemicals desired to be mixed together will produce a mixture or reaction mixture which is at least controllably exothermic under the conditions and in the manner in which the mixing is desired to be carried out.

The method invention comprises at least three steps when dealing with chemicals from a plurality of sources. Prior to mixing the chemicals as desired, the first step is flowing a known amount of chemicals from each of the chemical sources through separate, enclosed fluid communication means directly into a sealed calorimeter wherein the exothermic properties of the resulting mixtures are capable of being determined. Flowing the chemicals directly into the calorimeter greatly reduces the risk of exposure to personnel.

The second method step is to activate and observe the calorimeter.

The third method step is to determine from the calorimeter measurements if mixing the chemicals from the separate sources would result in a mixture which would be exothermically controllable. If this determination is positive, then the mix is made as desired. If the determination is negative, then other measures have to be taken.

Of course, there are many useful applications for the above method. As mentioned above the invention is quite useful where chemicals are desired to be dumped from a waste transport means such as a truck or pipeline into a chemical waste repository. In this event there are usually only two chemical sources, the chemical waste transport means and the chemical waste repository. After the calorimeter measurements are made the contents of the calorimeter can be emptied into the waste repository inasmuch as they have already undergone whatever reaction they are going to undergo in the calorimeter, and, hence, are now safe to place in the waste mixture. When dealing with many unknown waste chemicals in this two source situation, it is preferred to place an equal amount of chemicals from the waste repository with an equal amount of chemicals from the waste transport means in the calorimeter. This gives the most likely chance of detecting the most heat which can be generated by the mixture.

Another application of this system is the mixing of chemicals going into non-waste, production mixtures or reaction mixtures. Usually these chemicals and catalysts are already known and vary little in proportion or composition. In this instance calorimeter monitoring is often unnecessary. But sometimes there are sufficient variations occurring in the composition and proportion of the different chemical feeds to warrant calorimeter checks as herein described.

BRIEF DESCRIPTION OF THE DRAWINGS

The invention will be better understood by reference to the drawings wherein:

FIG. 1 is a schematic (not drawn to scale) of an on-site calorimeter test for a truck which is delivering waste chemicals to a waste chemical storage tank for disposal by later thermal oxidation in a furnace;

FIG. 2 is an enlarged schematic of the calorimeter 20 used in FIG. 1;

FIG. 3 is a schematic of a plurality of chemical feed lines running into a common header.

DETAILED DESCRIPTION OF THE EMBODIMENTS OF THE DRAWING

Referring to FIG. 1, truck 10 contains organic chemical waste which it has brought to waste chemical storage tank 12 to dump them there. Prior to dumping in tank 12, the truck's drainage hose 14 is connected to pipeline 16 with all valves of the system closed. Pipeline 16 has a small pipe 18 running from it to calorimeter 20. The details of calorimeter 20 can be seen by reference to FIG. 2. Pipeline 18 has cut-off valve 22 in it. Similarly calorimeter 20 has pipeline 24 running to it from tank 12. Line 24 has cut-off valve 26 in it. Running from calorimeter 20 to main pipeline 16 and thereby to storage tank 12 are calorimeter drainage pipelines 28 and 30. Lines 28 and 30 have valves 32 and 34 located in them, respectively. Situated in line 16 between the truck 10 and tank 12 is cut-off valve 36 and pump 38. The location of valve 36 and pump 38 along pipeline 16 is important. Valve 36 is located in line 16 between the site where line 18 leaves line 16 and the sites where lines 28, 30 enter line 16. Pump 38 is located between tank 12 and the site where lines 28, 30 enter line 16.

To operate the system as preferred, valves 26 and 40 (FIG. 2) are opened, and chemicals from waste tank 12 are flowed by gravity into calorimeter 20 until it is full. The calorimeter 20 is determined to be full when the chemicals reach the top of vent pipe 39. (The gravity flows described herein are not apparent from the drawing because of the location of calorimeter 20 in the drawing. In practice it is located where the gravity flows herein described work quite well, thereby avoiding the use of more pumps.)

While chemicals from tank 12 are flowed into sealed calorimeter 20, air is vented from calorimeter 20 via line 39 and valve 40 (FIG. 2). After calorimeter 20 is filled with chemicals from tank 12, valve 26 is closed to stop this inward flow and valve 32 is opened and pump 38 is activated to drain calorimeter 20 down to the level of the top of pipe 28 inside the calorimeter. The chemicals drained from calorimeter 20 are pumped back into tank 12 by pump 38 and then pump 38 is cut off and valve 32 is closed.

Thus, the amount of chemicals from tank 12 present in calorimeter 20 is determined by the height of the top of pipe 28 inside calorimeter 20. It is preferred to have the top of pipe 28 midway up inside calorimeter 20 so that the calorimeter will contain a chemical mix made up of equal portions of chemicals from tank 12 and truck 10 when the calorimetric measurements are made.

Next, valve 22 is opened and chemicals from truck 10 are gravity flowed into the top half of calorimeter 20 via hose 14, line 16 and line 18. Then valves 22 and 40 are closed, and agitator 42 mixes the two sets of chemicals inside the sealed calorimeter 20 while thermocouple 44 and backup thermocouple 46 measure the increase in heat and temperature, if any. These two thermocouples 46 and 48 are connected to a recorder (not shown) from which observations can be made concerning any changes in temperature occurring in the new mixture in the calorimeter 20.

After these observations are made then the decision is made as to whether it is safe to empty all the contents of truck 10 into tank 12. One procedure to follow when using relative unskilled personnel in making this decision is simply not to permit the truck to dump its chemicals into the tank whenever the calorimeter measurements show any increase in temperature. When there is some increase in temperature, more skilled personnel are required to determine if a safe dump can be made. For example, not only does the amount of temperature increase have to be considered, but also so do the rate of temperature increase, the heat dissipation capability of the tank, the flowrate into the tank, etc.

In any event, whether the decision is to dump or not to dump, the contents of calorimeter 20 can be discharged into tank 12. This discharge is accomplished by opening valves 40 and 34, turning on pump 38, and pumping the contents of calorimeter 20 into tank 12 via line 30 and line 16.

For the above described purposes, a 10 gallon calorimeter tank made of carbon steel has proved most beneficial.

Referring to FIG. 3, a more general system of the invention can be observed in the schematic diagram of it therein shown. Pipelines 50, 52, and 54 are seen connected to pipeline header 56 through valves 58, 60, and 62, respectively. Header 56 has a cut-off valve 64 located upstream from where lines 50, 52, and 54 tie into header 56. Each pipeline, 50, 52, and 54 has a valve (valves 58, 60, and 62 respectively) located in them at a site which is upstream from where they, the pipelines 50, 52, and 54 are connected to header 56.

Up stream from the valves 58, 60, 62, and 64, along their respective pipes 50, 52, 54, and 56, are located conduits 66, 68, 70, and 72 which connect their respective pipes 50, 52, 54, and 56 in fluid communication with sealed calorimeter 73 through respective cup-off valves 74, 76, 78, and 80 in said conduits 66, 68, 76, and 72.

Pipe 82 and valve 84 form the drainage outlet for calorimeter 73. This drainage outlet may lead to a separate dump (not shown) or it might feed back into one of the chemical sources, here pipes 50, 52, 54, and 56. Preferably it would connect back into header source pipe 56 at a site downstream from valve 64.

The present discussion of FIG. 3 assumes that header pipe 56 has a chemical stream flowing through it whether or not there is any chemical feed from lines 50, 52, and 54 into header pipe 56. In another situation this assumption will be untrue, and thus line 56 will not be a separate chemical source. Therefore line 72 and valve 80 would not be useful. For the present discussion, however, separate chemicals will be assumed to be desired to be flowed in all four pipes, pipes 50, 52, 54, and 56 with mixing of all chemicals taking place in header 56.

The method of operation of this system to determine if the mixture desired to be made of all four sets of chemicals in pipe 56 goes as follows; initially valves 58, 60, 62, and 64 are closed and valves 74, 76, 78, and 80 are opened so that chemicals from each chemical source, pipes 50, 52, 54, and 56 directly and separately into calorimeter 73 via pipes or conduits 66, 68, 70, and 72 respectively. Preferably known amounts of the chemicals from each source pipes 50, 52, 54, and 56 are flowed in calorimeter 73. If the observed calorimeter measurements indicate a safe mixture is possible then this mixing is allowed to occur by the following procedure. Valves 74, 76, 78, and 80 are closed and valves 58, 60, 62, and 64 are opened to allow the chemicals to flow in pipes 50, 52, 54, and 56 as the arrowheads on these pipes indicate.

I claim:

1. A system capable of determining if waste chemicals from a chemical waste transport vessel can be safely emptied into a chemical waste collection vessel already containing an unidentified mixture of waste chemicals without having a run-away exothermic reaction within the chemical waste collection vessel, said system being comprised of:
   (A) a chemical waste collection vessel containing an unidentified mixture of waste chemicals;
   (B) a chemical waste transport vessel containing waste chemicals which are desired to be emptied into the chemical waste collection vessel if no run-away exothermic chemical reaction will occur upon the mixing of the chemicals from the chemical waste transport vessel with the chemicals in the chemical waste collection vessel;
   (C) a sealed calorimeter;
   (D) means for connecting each of said separate vessels with said sealed calorimeter in a manner so that a known sample amount of chemicals from each vessel can be flowed into said calorimeter in order to determine if the chemicals can be mixed in the manner and under the conditions desired without having run-away exothermal reaction in the waste collection vessel; and
   (E) means for transferring the bulk of the waste chemicals directly from the chemical waste transport vessel into the chemical waste collection vessel without passing through the calorimeter if the calorimeter has already indicated that the waste chemicals from the transport vessel can be safely mixed with those in the collection vessel; but said system not containing a means for identification and classification of the unidentified mixture of waste chemicals contained in the chemical waste collection vessel.

2. The system of claim 1 wherein the calorimeter is further comprised of a chemical drainage pipe which extends about one-half way up the interior of the calorimeter test volume so that about equal sample amounts of the chemical wastes from the collection vessel and the transport vessel can be mixed and tested in the calorimeter by first filling the calorimeter from one of the vessels, then draining the calorimeter of this chemical through the pipe which extends half-way upward in the mixing volume of the calorimeter until it ceases to drain so as to leave the calorimeter volume one-half full of chemicals from this vessel and simultaneously leave about an equal volume in the calorimeter for chemicals from the other vessel to be added and mixed in the calorimeter with the chemicals from the first vessel.

3. The system of claim 2 wherein the pipe which drains the chemicals from the calorimeter is in fluid communication with means for draining the calorimeter directly into the chemical waste collection vessel.

* * * * *